United States Patent [19]

Yamamoto et al.

[11] Patent Number: 5,429,591
[45] Date of Patent: Jul. 4, 1995

[54] ABSORBENT DRESSING HAVING BACKING AND CONTINUOUS ADHESIVE LAYER

[75] Inventors: Katsuhiro Yamamoto; Tetsuo Watanabe; Toshiyuki Yamamoto, all of Osaka, Japan

[73] Assignee: Nitto Denko Corporation, Osaka, Japan

[21] Appl. No.: 102,503

[22] Filed: Aug. 5, 1993

Related U.S. Application Data

[63] Continuation-in-part of Ser. No. 916,710, Jul. 22, 1992, abandoned.

[30] Foreign Application Priority Data

Jul. 22, 1991 [JP] Japan ............................ 3-206510
May 28, 1992 [JP] Japan ............................ 4-164078

[51] Int. Cl.⁶ .................... A61F 13/00; C08L 15/00
[52] U.S. Cl. ............................. 602/54; 602/56; 602/900; 604/307; 604/336; 424/448; 523/111
[58] Field of Search ................... 602/54, 56, 900; 604/307, 336; 424/448; 523/111

[56] References Cited

U.S. PATENT DOCUMENTS

| | | | |
|---|---|---|---|
| 2,969,057 | 1/1961 | Simmons | 604/307 |
| 3,339,549 | 9/1967 | Morse | |
| 4,362,841 | 12/1982 | Minatona et al. | 602/48 |
| 4,538,603 | 9/1985 | Pawelchak et al. | 602/54 |
| 4,706,662 | 11/1987 | Thompson | 602/57 |
| 4,753,231 | 6/1988 | Lang et al. | 602/47 |
| 4,871,490 | 10/1989 | Rosiak et al. | 602/900 |
| 4,909,243 | 3/1990 | Frank et al. | 602/304 |
| 5,092,323 | 3/1992 | Riedel et al. | 602/52 |

FOREIGN PATENT DOCUMENTS

| | | |
|---|---|---|
| 0092999 | 11/1983 | European Pat. Off. . |
| 0340945 | 11/1989 | European Pat. Off. . |
| 0352086 | 1/1990 | European Pat. Off. . |
| 58-190446 | 11/1983 | Japan . |
| 213463 | 1/1990 | Japan . |

*Primary Examiner*—Paul Prebilic
*Attorney, Agent, or Firm*—Sughrue, Mion, Zinn, Macpeak & Seas

[57] ABSTRACT

A dressing comprising a backing and an adhesive layer, wherein the backing is moisture-permeable and the adhesive layer comprises an adhesive composition comprising a rubber-based adhesive, a polymer having a water-absorbing property and/or a water-swelling property, and a metal oxide and/or a metal salt, the polymer having the water-absorbing property and/or the water-swelling property being a polymer containing a functional group having an ability to form a salt and/or coordination compound.

9 Claims, 6 Drawing Sheets

ABSORBENT DRESSING HAVING BACKING AND CONTINUOUS ADHESIVE LAYER

This is a Continuation-In-Part of application Ser. No. 07/916,710, filed Jul. 22, 1992, now abandoned.

FIELD OF THE INVENTION

The present invention relates to a dressing which can be used in various medical applications, especially in the fields of dressing for wounds and treatments of incontinence and artificial anuses, and is particularly effective against wounds difficult to remedy, such as chronic skin ulcers.

BACKGROUND OF THE INVENTION

Hydrocolloid-containing adhesive compositions have been known for many years.

One example of such compositions is disclosed in U.S. Pat. No. 3,339,549 by Chen. This hydrocolloid-containing adhesive composition comprises a rubber elastomer, such as polyisobutylene, and one or more water-soluble or water-swelling hydrocolloids, such as a powdery mixture of pectin, gelatin, and carboxymethyl cellulose.

In this hydrocolloid-containing adhesive composition, the rubber elastomer provides adhesion properties and the hydrocolloid powder particles function to absorb exudates from wounds or sweat.

Use of such hydrocolloid-containing adhesive compositions in bandages for skin ulcers, burns, and other exudative wounds is gradually arousing attention.

For example, an occlusive multilayered bandage comprising a polymer film impermeable to external water, an intermediate layer which is a semi-open-cell polymer foam layer provided on one side of the polymer film, and an adhesive layer formed on the intermediate layer is proposed in JP-A-58-190446. (The term "JP-A" as used herein means an "unexamined published Japanese patent application".) This multilayered bandage is characterized in that the adhesive layer consists essentially of a homogeneous blend of one or more pressure-sensitive adhesive materials which may contain, if required and necessary, one or more thermoplastic elastomers with one or more water-dispersible hydrocolloids which may contain, if required and necessary, one or more water-swelling flocculating reinforcements and/or one or more polymers having hydrating properties.

However, this hydrocolloid-containing adhesive composition layer has a drawback that when the dressing is applied to a wounded part of the body, the adhesive layer swells as it absorbs an exudate from the wound and other body fluids, and the adhesive layer finally suffers a separation between components. This means that the rubber elastomer (rubber-based adhesive) which has served to bond hydrocolloid particles together is dispersed and comes to be present as dispersed independent particles.

As a result of the decrease of the interaction between the components constituting the hydrocolloid-containing adhesive composition layer, not only the adhesive layer loses the shape retention property to allow part of the adhesive composition to flow out from the substrate, but also the adhesion of the adhesive layer decreases at the edge parts of the applied dressing. Thus, the dressing comes to be unable to perform its function as a dressing.

Although the above problem may be overcome by increasing the strength of the rubber-based adhesive, the use of a rubber-based adhesive having an increased strength in an adhesive layer of the above-described type may cause a problem that when the adhesive layer is contacted with an exudate from a wound and with other body fluids, the hydrocolloid particles cannot swell sufficiently and, hence, the adhesive layer has a poor absorbing capacity.

For the above reason, use of special hydrocolloids (polymers) having the property of absorbing water and/or swelling in water is being studied recently.

For example, JP-A-2-13463 proposes use of hydrocolloid particles comprising particles of a polycationic hydrocolloid and particles of a polyanionic hydrocolloid.

In the above JP-A, water-soluble chitosan salts such as chitosan maleate and chitosan glutarate are enumerated as examples of the polycationic hydrocolloid, and pectin, carboxymethyl cellulose, alginic acid salts, and the like are enumerated as examples of the polyanionic hydrocolloid.

In dressings using such polycationic and polyanionic hydrocolloid particles, the combining force among hydrocolloid particles may be improved to some degree due to the use of the two kinds of hydrocolloid particles. However, these dressings have drawbacks that the adhesion of the adhesive layer to the body becomes low upon absorption of an exudate or body fluids and that part of the hydrocolloid-containing adhesive composition dissolves in the absorbed fluids and flows out from the backing.

SUMMARY OF THE INVENTION

It has been found that when a dressing having an adhesive layer comprising an adhesive composition which comprises a rubber-based adhesive, a polymer having a water-absorbing property and/or a water-swelling property, and powder particles of a metal oxide and/or metal salt and in which the polymer having the water-absorbing property and/or the water-swelling property is a polymer containing a functional group having the ability to form a salt and/or to coordinate (i.e., from a coordination compound) is applied to a wounded site or other site of the body and the adhesive layer absorbs an exudate from the wound and other body fluids, the polymer having the water-absorbing property and/or the water-swelling property forms ionic or coordinate bonds to metal ions generated from the metal oxide and/or metal salt, and the formation of such ionic or coordinate bonds serves to improve the adhesion of the adhesive composition, to maintain the shape retention property of the adhesive layer, to prevent the adhesive composition from dissolving into body fluid or flowing out, and to enable the adhesive layer to efficiently absorb an exudate and other body fluids and hold the absorbed liquids therein. In order to overcome the technical problems described hereinabove, the present invention has been completed based on the above finding.

Accordingly, an object of the present invention is to provide a dressing comprising a backing and an adhesive layer, wherein the backing is moisture-permeable and the adhesive layer comprises an adhesive composition comprising a rubber-based adhesive, a polymer having the water-absorbing property and/or the water-swelling property, and a metal oxide and/or a metal salt, and the polymer having the water-absorbing property and/or a water-swelling property is a polymer containing a functional group having the ability to form a salt and/or to coordinate.

DETAILED DESCRIPTION OF THE INVENTION

Figure 1:
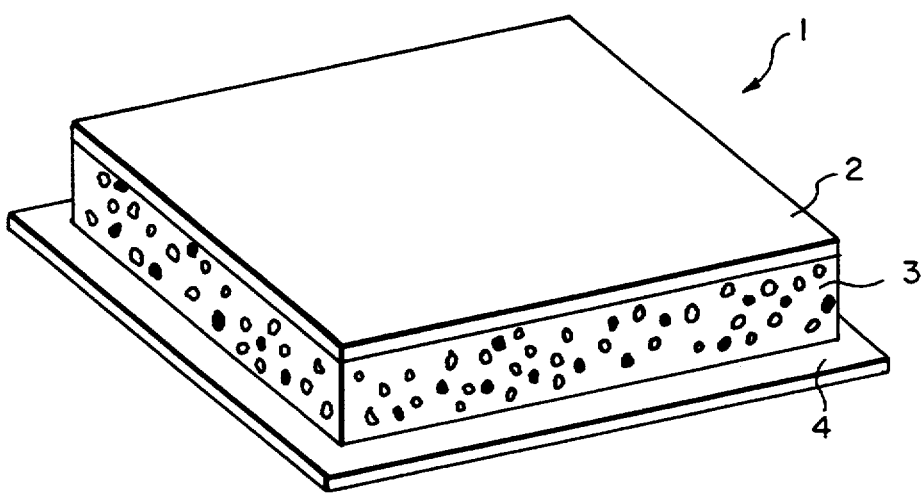
FIG. 1 is a perspective view showing one embodiment of the dressing according to the present invention.

The backing used in the dressing of the present invention is not particularly limited, and examples thereof include films or sheets made of polyolefins, polyesters, polyurethanes, polybutadiene, polyamides, acrylic copolymers, or the like and nonwoven or woven fabrics made of polyesters, acetates, or the like. It is, however, necessary to use a backing which is moisture-permeable. To make a backing porous is advantageous in that not only moisture permeability is ensured but also stretchability can be imparted to the backing. Of the backing materials described above, polyether polyurethanes, polyether-polyamide block polymers, and the like are advantageously used as stretchable materials. In order to impart bacteria-barrier properties and virus impermeability to the dressing, use of a porous backing having no open cells is preferred. Further, it is preferred that the backing is in the form of a film having a thickness of about from 10 to 100 $\mu$m, preferably about from 20 to 80 $\mu$m. If the backing has a thickness below 10 $\mu$m, the dressing has poor mechanical strength or handling properties. If the thickness of the backing exceeds 100 $\mu$m, the dressing shows poor fitness and comfort to the body or has poor handling properties or moisture permeability. From the standpoint of attaining good handling properties and hand feeling, use of a multilayered backing is preferred which comprises a film or sheet of any of the above-described kinds and a nonwoven or woven fabric laminated therewith on the side opposite the side where an adhesive layer is to be formed.

It is preferred that the backing has a moisture permeability of from 300 to 5,000 g/m$^2$·24 hr, preferably from 500 to 2,000 g/m$^2$·24 hr. Moisture permeabilities as low as below 300 g/m$^2$·24 hr are not preferred in that when the dressing is kept applied to the body for a long time period, evaporation of the water that has absorbed by the adhesive layer is diminished due to the low moisture permeability of the backing and, as a result, the adhesive layer changes in composition and part of the adhesive layer becomes more apt to flow out. On the other hand, moisture permeabilities exceeding 5,000 g/m$^2$·24 hr are not preferred in that the surface of the wounded part to which the dressing has been applied dries excessively due to the high moisture permeability of the backing and, as a result, cure of the wound is retarded. In the present invention, measured values of moisture permeability are obtained by the Payne cup method.

The adhesive layer in the dressing of the present invention comprises an adhesive composition having the property of water-absorbing and/or the property of water-swelling. This adhesive composition comprises a rubber-based adhesive, a polymer having the water-absorbing property and/or the water-swelling property, and a metal oxide and/or a metal salt, and the polymer having the water-absorbing property and/or the water-swelling property contains a functional group having the ability to form a salt and/or to coordinate.

In general, the adhesive layer is formed at a thickness of from 10 to 4,000 $\mu$m. It is preferable that the thickness of the adhesive layer is about from 10 to 1,000 $\mu$m when the dressing is applied to a wound from which an exudate is oozing out in a relatively small amount, and is about from 1,000 to 4,000 $\mu$m when the dressing is applied to a wound from which an exudate is oozing out in a relatively large amount. Small adhesive layer thicknesses are preferred in that the dressing of the present invention can have transparency and, hence, the wound to which the dressing has been applied can be examined visually without the necessity of stripping off the dressing.

Examples of the rubber-based adhesive used in the adhesive layer include adhesives containing polyisobutylene, natural rubber, a polyurethane, a styrene-isoprene-styrene teleblock polymer, an acrylic polymer, poly(vinyl acetate), an ethylene-Vinyl acetate copolymer, or the like as a main component. It is necessary to use a rubber-based adhesive which has elasticity sufficient to fully relax a stress resulting from the water absorption and swelling of the polymer which is present in the adhesive layer along with the rubber-based adhesive and has the water-absorbing property and/or the water-swelling property. The rubber-based adhesive preferably is an adhesive which contains polyisobutylene as the base polymer for the adhesive, particularly an adhesive containing a relatively low molecular weight polyisobutylene having a viscosity-average molecular weight of about from 30,000 to 100,000. From the standpoint of imparting cohesive force to the adhesive layer thereby to enable the adhesive layer to maintain the shape retention property and to be free from the problem that part of the adhesive is squeezed out from a side of the adhesive layer, it is preferred that a high molecular weight polyisobutylene having a viscosity-average molecular weight of from 900,000 to 2,000,000 is added, along with the low molecular weight polyisobutylene described above, in an amount of from 5 to 20% by weight based on the weight of the rubber-based adhesive.

It is preferred to sterilize the adhesive layer by subjecting the adhesive layer to irradiation treatment such as irradiation with $\gamma$-rays or electron beams. However, where the rubber-based adhesive contains polyisobutylene, it is known that the backbones of the polyisobutylene may be decomposed by irradiation, causing the adhesive composition possibly to liquefy and flow out. Therefore, in order to prevent such a phenomenon, it is preferable that a polymer which, upon irradiation, undergoes not a degradation reaction but a crosslinking reaction, such as natural rubber, polyisoprene, polybutadiene, polyethylene, polypropylene, an ethylene-propylene copolymer, or the like, is added to the adhesive layer in an amount of from 2 to 50% by weight, preferably from 3 to 20% by weight, based on the weight of the rubber-based adhesive. Preferred of these irradiation-crosslinkable polymers are polyisoprene, polybutadiene, and polyethylene. In particular, use of polyisoprene, especially high-cis-polyisoprene, having a viscosity-average molecular weight of about from 500,000 to 2,000,000, high-cis-1,4-polybutadiene, or low-density polyethylene having a melt flow index (in accordance with ASTM D-1238) of from 20 to 80 is preferred. If the amount of the irradiation-crosslinkable polymer added is below 2% by weight, the addition thereof cannot produce a sufficient effect. The amounts thereof added exceeding 50% by weight are also not preferred in that such an adhesive layer has poor flexibility and, as a result, the adhesive layer may hurt the wound to which the dressing is to be applied or may weaken the water-absorbing or water-swelling properties of the polymer which has the water-absorbing property and/or the water-swelling property and is present along with the rubber-based adhesive.

The polymer having the water-absorbing property and/or the water-swelling property, which is added to the adhesive layer in the dressing of the present invention, is a polymer containing a functional group having the ability to form a salt and/or to coordinate. As this polymer, a polymer which, when immersed in physiological saline, shows high saline penetrability and high saline-absorbing capacity is employed. Examples of the polymer include gelatin, pectin, carboxymethyl cellulose (and its sodium salt), alginic acid (and its sodium salt), glucomannan, xanthine gum, locust bean gum, carrageenan, methyl vinyl ether-maleic anhydride copolymers, and acrylic acid-vinyl alcohol copolymers. Examples thereof further include so-called highly water-absorbing polymers such as starch-acrylic acid graft polymers, acrylic acid-acrylamide copolymers, and crosslinked carboxymethyl cellulose. These polymers can be used alone or in combination of two or more thereof. It is a matter of course that a polymer which does not contain a functional group having the ability to form a salt or to coordinate, such as karaya gum, guar gum, poly(ethylene glycol), polyacrylamide, poly(vinyl alcohol), a starch-acrylonitrile graft polymer, or crosslinked dextrin, can be used in combination with the polymer containing a functional group having the ability to form a salt and/or to coordinate.

The metal oxide and/or metal salt contained in the adhesive composition is one which, when the adhesive layer of the dressing applied to a wound absorbs an exudate from the wound or body fluids, releases metal ions which form ionic or coordinate bonds to the polymer having the water-absorbing property and/or the water-swelling property. The metal ions should have a valence of 2 or more. The metal salt consists of a water-soluble metal salt alone, a sparingly-water-soluble metal salt alone, or a combination thereof. Where the water-soluble metal salt is added, the adhesive composition quickly combines by absorption of exudates in the adhesive layer. On the other hand, where the sparingly-water-soluble metal salt is added, the adhesive composition gradually combines to maintain a sustained combined state. In the present invention, the term "water-soluble metal salt or metal oxide" is defined that 5 g or more of a metal salt or metal oxide dissolves in 100 g water, while the term "sparingly-water-soluble metal salt or metal oxide" is defined that less than 5 g of a metal salt or metal oxide dissolves in 100 g water.

Examples of the water-soluble metal salt include aluminum salts such as alum, burnt alum (anhydrous alum), aluminum sulfate, aluminum lactate, aluminum salicylate, and aluminum nitrate and other metal salts such as calcium chloride, iron chloride, copper sulfate, and barium chloride. These can be added alone or in combination of two or more thereof.

Examples of the sparingly-water-soluble metal salt, a metal hydroxide or metal oxide include aluminum hydroxide, aluminum phosphate, aluminum citrate, aluminum benzoate, calcium hydroxide, calcium citrate, calcium carbonate, calcium oxalate, calcium phosphate, calcium tartrate, zinc citrate, calcium oxide, aluminum oxide, zinc oxide, copper oxide, silver oxide, titanium oxide, silver chloride, barium sulfate, and calcium sulfite. These can be used alone or in combination of two or more thereof.

From the standpoint of attaining good absorption of exudates from wounds, it is preferred that both the polymer having the water-absorbing property and/or the water-swelling property and the metal oxide and/or metal salt are added to the adhesive layer in the form of a powder. In general, an average particle diameter of those powders is from 1 to 1,000 $\mu$m, preferably from 1 to 300 $\mu$m. If transparency of the dressing is required, an average particle diameter of the powders is 50 $\mu$m or less.

In the adhesive layer in the dressing of the present invention, the proportion of each component added is specified below from the standpoints of the adhesion of the adhesive layer to the body, the rate of water absorption or swelling upon water absorption, the amount of water to be absorbed by the adhesive layer, and the shape retention property of the adhesive layer. The relative amounts of the rubber-based adhesive (A), the polymer having the water-absorbing property and/or the water-swelling property (B), and the metal oxide and/or metal salt (C) are such that the proportion of (A)/(B)/(C) is generally 30–80/20–65/0.5-20 by weight, preferably 40–60/30–60/2-10 by weight.

If required and necessary, a plasticizer, a tackifier resin, and the like can be arbitrarily added to the adhesive layer in an amount of about from 5 to 60% by weight based on the weight of the rubber-based adhesive, in order to improve adhesion properties. Examples of the plasticizer include paraffinic oils, polybutene, alcohols, and fatty acid esters. Examples of the tackifier resin include hydrocarbon resins, alkylphenol resins, terpene resins, terpene-phenolic resins, ester gums, and hydrogenated ester gums.

Further, an antibacterial agent, such as hibitene, chlorohexydine gluconate, benzalkonium chloride, benzethonium chloride, Povidone Iodine, iodine and potassium iodide, sulfadiazine silver, or a sulfa drug, and an antibiotics, such as furadiomicine sulfate or gentamisine sulfate, can also be added to the adhesive composition. These can be added alone or in combination of two or more thereof in an amount of generally from 0.01 to 20% by weight, preferably from 0.05 to 5% by weight, based on the weight of the adhesive layer. Addition of the antibacterial agent or antibiotics is effective in sterilizing the body part to which the dressing is applied and in preventing multiplication of bacteria.

Due to the above-described construction of the dressing of the present invention, when the dressing is applied to the body at its wounded part or other part, the adhesive layer of the dressing rapidly absorbs an exudate from the wound or other body fluids and, as a result, metal ions are released from the metal oxide or metal salt contained in the adhesive layer and the metal ions form ionic or coordinate bonds to the polymer having the water-absorbing property and/or the water-swelling property, thereby improving the adhesion of the adhesive layer and enabling the adhesive layer to exhibit its water-absorbing or swelling ability while maintaining the shape retention property which is a property originally possessed by the adhesive layer.

The present invention will be explained below in more detail by reference to the accompanying drawings.

Figure 2:
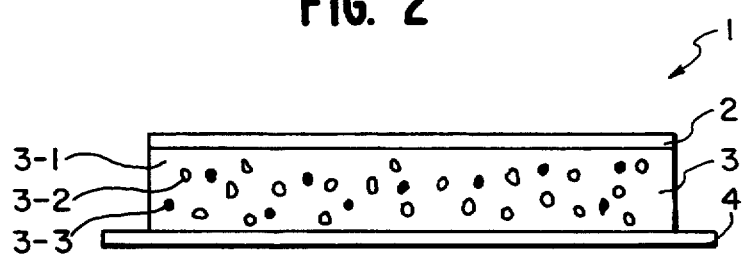
FIG. 2 is a sectional view of the dressing of FIG. 1.

In FIGS. 1 and 2, the dressing 1 according to the present invention comprises a backing 2 and an adhesive layer 3 formed on one side of the backing 2 and comprising an adhesive composition. A separator 4 covers the exposed surface of the adhesive layer 3.

In FIG. 2, the continuous phase in the adhesive layer 3 comprises a rubber-based adhesive 3-1, while the dispersed phase dispersed in the continuous phase comprises a polymer 3-2 having the water-absorbing property and/or the water-swelling property (shown by open circles in the figure) and a metal oxide and/or metal salt 3-3 (shown by solid circles in the figure).

It should be noted that when a side of the adhesive layer of the dressing of the invention is brought into direct contact with water, e.g., where the person to whom the dressing has been applied takes a bath, the adhesive layer swells at the edge part, resulting in a problem that the swollen part of the adhesive layer may foul clothes or the dressing becomes apt to peel off the body.

Figure 3:
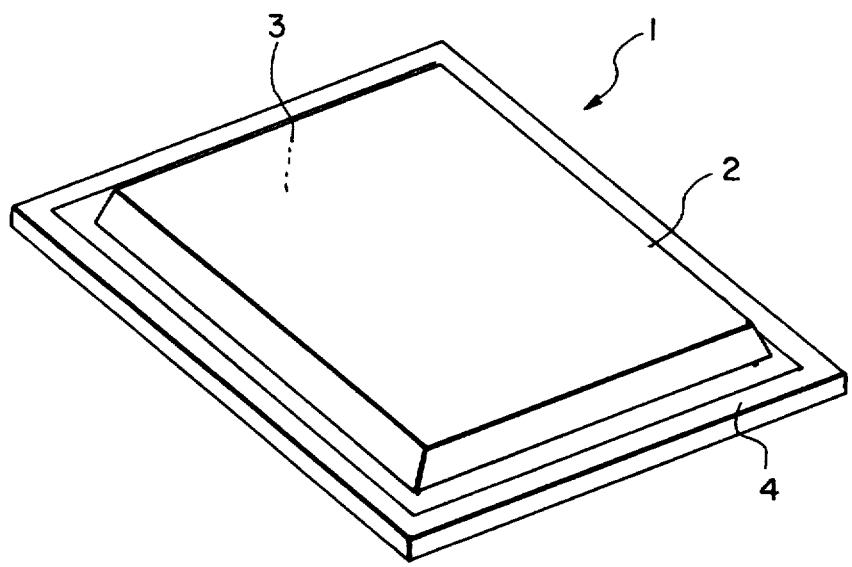
FIG. 3 is a perspective view showing another embodiment of the dressing according to the present invention.
Figure 4:
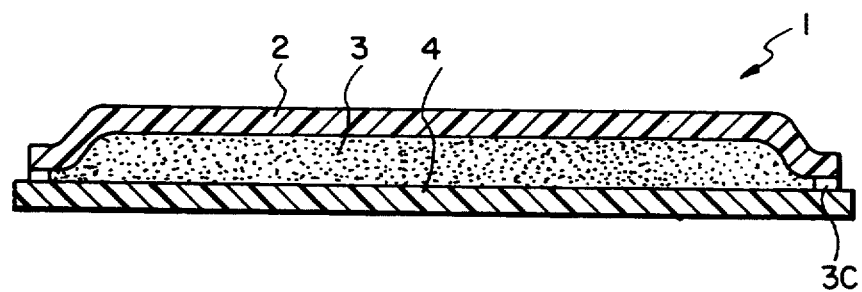
FIG. 4 is a sectional view of the dressing of FIG. 3.

In such a case, external penetration of water can be prevented by, as shown in FIG. 3 (perspective view) and FIG. 4 (sectional view), making the backing 2 have a larger size than the adhesive layer 3 and cover the upper surface and side parts of the adhesive layer 3 and further making the separator 4 have a larger size than the adhesive layer 3. As shown in FIG. 4, an edge part 3c of the backing 2 is bonded to an edge part of the separator 4 by a thinned part of the adhesive layer 3. It is preferred that the width of the edge part 3c in FIG. 4 is 5 mm or less and the thickness of the part of adhesive layer 3 in contact with the edge part 3c is regulated at around from 10 to 100 μm.

Figure 5:
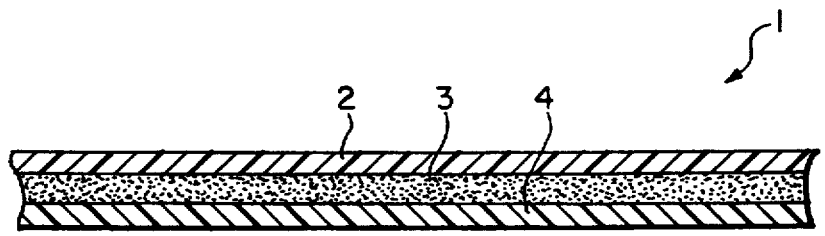
FIGS. 5 to 7 show one example of the production of the dressing according to the present invention.
Figure 6:
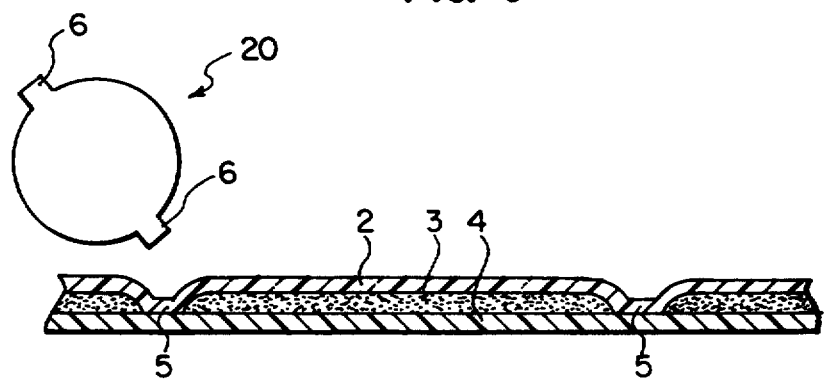
Figure 7:
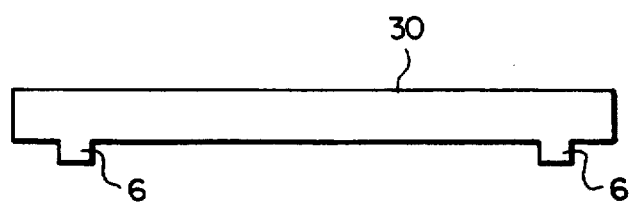
Figure 8:
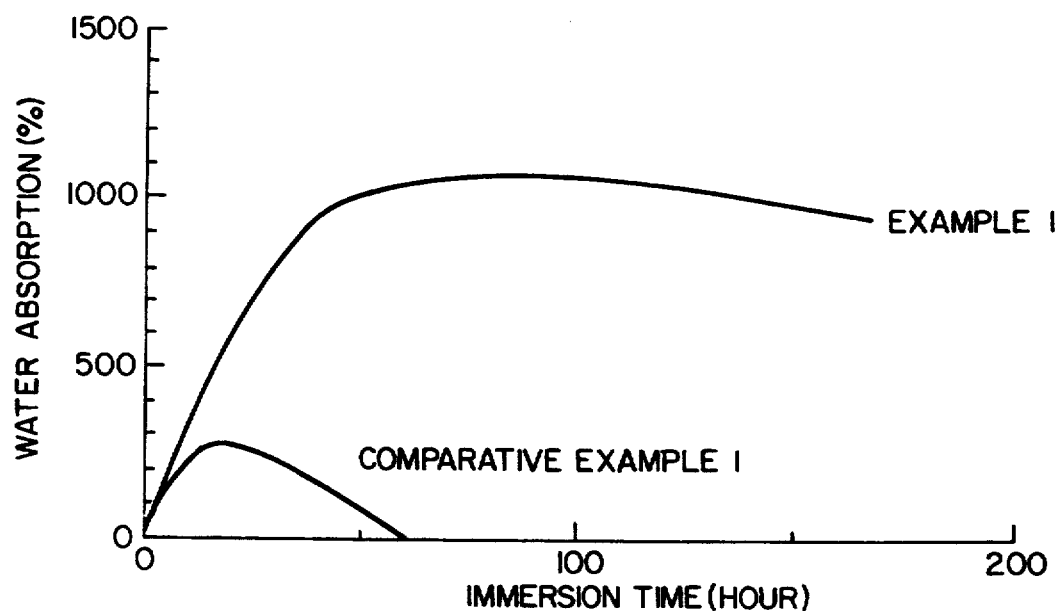
FIG. 8 is a graph showing absorption characteristic in physiological saline of the dressings obtained in Example 1 and Comparative Example 1.
Figure 9:
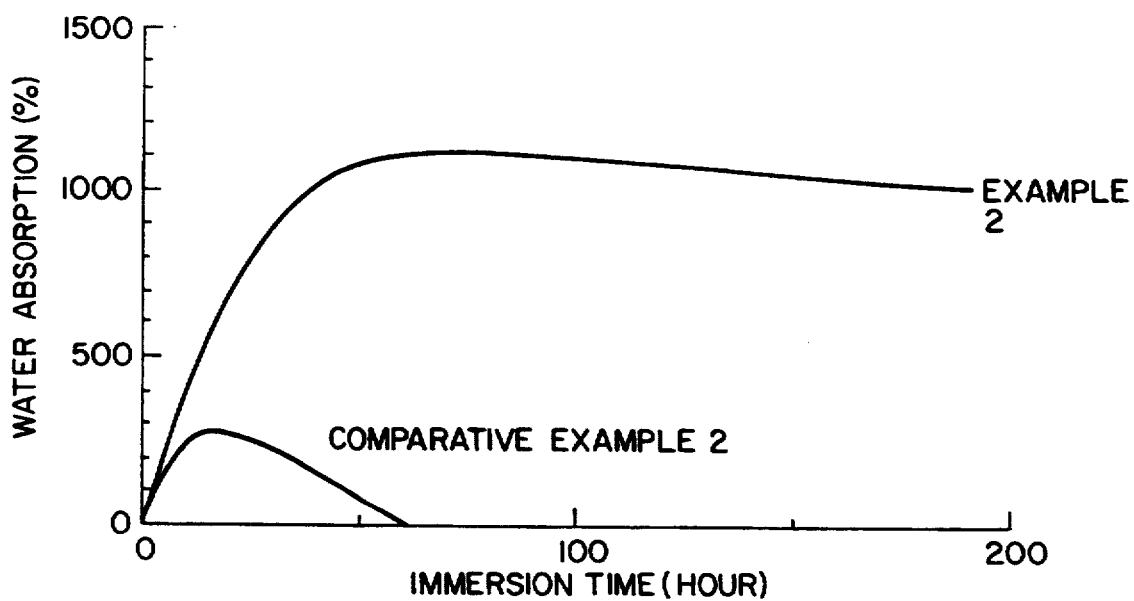
FIG. 9 is a graph showing absorption characteristic in physiological saline of the dressings obtained in Example 2 and Comparative Example 2.
Figure 10:
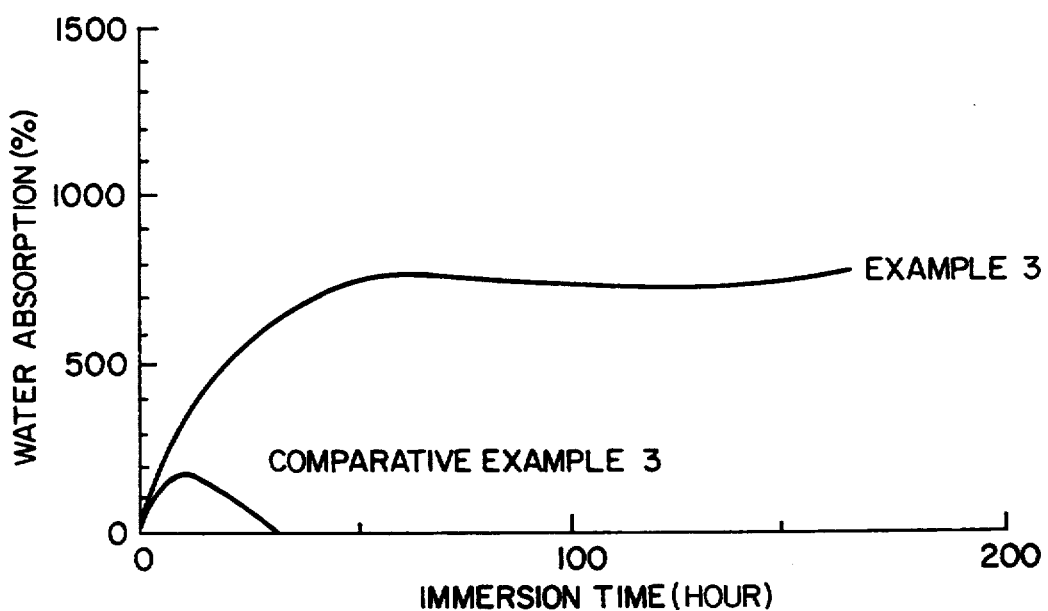
FIG. 10 is a graph showing absorption characteristic in physiological saline of the dressings obtained in Example 3 and Comparative Example 3.
Figure 11:
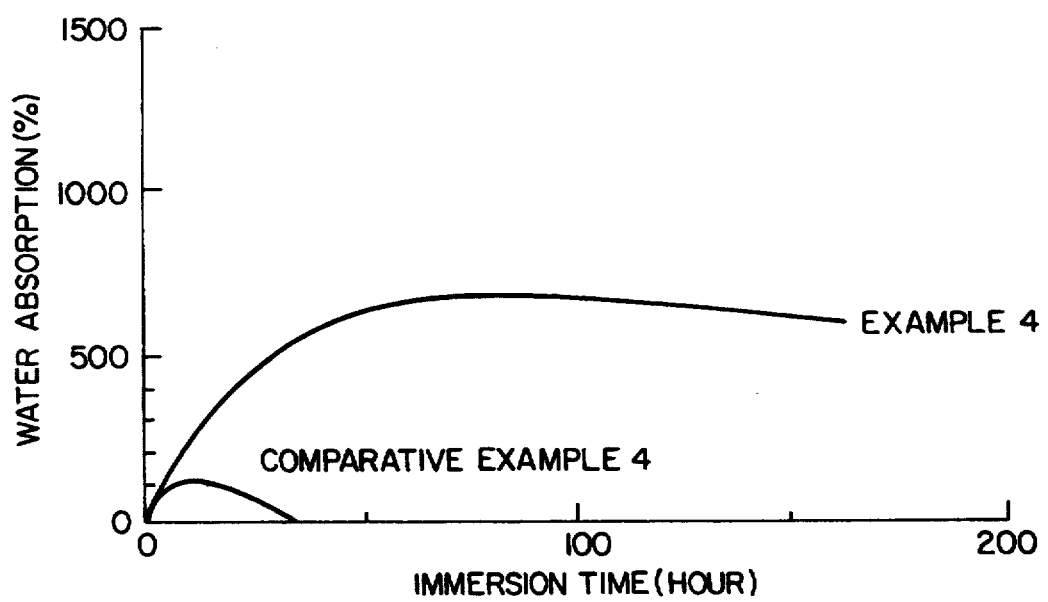
FIG. 11 is a graph showing absorption characteristic in physiological saline of the dressings obtained in Example 4 and Comparative Example 4.

Preferred embodiments of the production method for the dressing of the present invention are explained below by reference to FIGS. 5 to 7.

First, an adhesive composition is shaped into a sheet by, for example, an extruder and the sheet is bonded to a backing 2 on one side thereof. The exposed surface of the resulting adhesive layer on the backing 2 is covered with a separator 4, thereby to prepare a three-layer structure 10 in continuous form as shown in FIG. 5. This three-layer structure 10 is then pressed with a roller press 20 having a projection 6 as shown in FIG. 6, thereby to make a groove 5 in the three-layer structure 10. In place of this roller press 20, another pressing machine such as a platen press 30 having a projection 6 as shown in FIG. 7 can be used. The formation of the groove 5 is conducted either continuously or batchwise. In making such grooves, it is preferred to regulate the pressing force at a value such that the thickness of the adhesive layer 3 is reduced to about from 10 to 100 μm at the grooved part.

The present invention will be explained below in more detail by reference to the following Examples and Comparative Examples, but the invention is not construed as being limited thereto.

EXAMPLE 1

Sodium salt of carboxymethyl cellulose, pectin, gelatin, potassium alum each in the form of a powder were mixed beforehand in respective amounts shown below. Thus, a powdery mixture of the polymers having the water-absorbing property and/or the water-swelling property and the metal salt was obtained.

| | |
|---|---|
| Na salt of carboxymethyl cellulose | 19.4 g |
| Pectin | 13.8 g |
| Gelatin | 21.5 g |
| Potassium alum | 3.3 g |

38.8 g of a low molecular weight polyisobutylene (viscosity-average molecular weight: 50,000) and 3.2 g of a high molecular weight polyisobutylene (viscosity-average molecular weight: 990,000) were sufficiently kneaded in a 150 ml kneader at 80° C. to prepare a rubber-based adhesive. Kneading of the adhesive was further continued while the powdery mixture obtained above was gradually added thereto, thereby obtaining an adhesive composition.

Using a hot press, the thus-obtained composition was press-formed into a sheet having a thickness of 1.5 mm. This sheet was then sandwiched between a backing (polyether polyurethane film 35 μm thick) and a separator that had undergone silicone treatment, thereby preparing a dressing according to the present invention.

EXAMPLE 2

A powdery mixture of polymers having the water-absorbing property and/or the water-swelling property, a metal oxide, and metal salts was obtained in the same manner as in Example 1 by mixing the following powders.

| | |
|---|---|
| Na salt of carboxymethyl cellulose | 17.5 g |
| Pectin | 17.5 g |
| Gelatin | 17.5 g |
| Potassium alum | 1.4 g |
| Aluminum hydroxide | 1.5 g |
| Aluminum oxide | 1.6 g |

39.7 g of a low molecular weight polyisobutylene (viscosity-average molecular weight: 50,000) and 3.3 g of a high molecular weight polyisobutylene (viscosity-average molecular weight: 990,000) were sufficiently kneaded in a 150 ml kneader at 80° C. to prepare a rubber-based adhesive. Kneading of the adhesive was further continued while the powdery mixture obtained above was gradually added thereto, thereby obtaining an adhesive composition.

In the same manner as in Example 1, the thus-obtained composition was press-formed into a sheet and this sheet was then sandwiched between a backing and a separator, thereby preparing a dressing according to the present invention.

EXAMPLE 3

A rubber-based adhesive was prepared by sufficiently kneading 39.1 g of a low molecular weight polyisobutylene (viscosity-average molecular weight: 50,000) and 3.9 g of a high-cis-polyisoprene (viscosity-average molecular weight: 900,000) in a 150 ml kneader at 80° C. Kneading of the adhesive was then further continued while the same powdery mixture as obtained in Example 2 was gradually added thereto, thereby obtaining an adhesive composition.

In the same manner as in Example 1, the thus-obtained composition was press-formed into a sheet and this sheet was sandwiched between a backing and a separator. Further, the adhesive layer was irradiated with γ-rays at a dose of 2.5 Mrad, thereby preparing a dressing according to the present invention.

EXAMPLE 4

A powdery mixture of polymers having the water-absorbing property and/or the water-swelling property, a metal oxide, and metal salts was obtained in the same manner as in Example 1 by mixing the following powders.

| | |
|---|---|
| Na salt of carboxymethyl cellulose | 8.0 g |
| Pectin | 17.0 g |
| Gelatin | 17.0 g |
| Crosslinked graft copolymer of starch and acrylic acid salt | 9.0 g |
| Potassium alum | 2.0 g |
| Aluminum hydroxide | 1.5 g |
| Aluminum oxide | 1.5 g |

37.6 g of a low molecular weight polyisobutylene (viscosity-average molecular weight: 50,000), 3.0 g of a high molecular weight polyisobutylene (viscosity-average molecular weight: 990,000), and 3.4 g of natural rubber were sufficiently kneaded in a 150 ml kneader at 80° C. to prepare a rubber-based adhesive. Kneading of the adhesive was further continued while the powdery mixture obtained above was gradually added thereto, thereby obtaining an adhesive composition.

The thus-obtained composition was press-formed into a sheet in the same manner as in Example 1, and the sheet was then sandwiched between a backing (a laminate of a polyester nonwoven fabric (basis weight: 30 g/m$^2$) with a polyether polyurethane film (thickness: 10 μm)) and a separator in a manner such that the backing came into contact with the adhesive layer on the polyurethane film side. Further, the adhesive layer was irradiated with γ-rays at a dose of 2.5 Mrad, thereby preparing a dressing according to the present invention.

EXAMPLE 5

An adhesive composition was obtained in the same manner as in Example 2 except that a 50 liter kneader was used. Using an extruder, the thus-obtained composition was extruded into a sheet having a thickness of 1.5 mm. This sheet was then sandwiched between a backing (polyether polyurethane film 35 μm thick) and a separator that had undergone silicone treatment.

Grooves having a width of 4 mm were formed on the above-obtained three-layer structure in a manner such that a dressing product to be obtained from the three-layer structure would have a size of 10 cm by 10 cm. This groove formation was conducted using heated rollers for press molding which had projections having a width of 4 mm. Thereafter, the resulting three-layer structure was cut along the center of each groove, thereby preparing a dressing according to the present invention.

EXAMPLE 6

The same powdery mixture as obtained in Example 2 was pulverized using a pulverizer, and the resulting powder was sieved to obtain a powdery mixture having an average particle diameter of 50 μm or less.

A dressing according to the present invention was then prepared in the same manner as in Example 2 except that the above-obtained powdery mixture was used.

COMPARATIVE EXAMPLE 1

A dressing was prepared in the same manner as in Example 1 except that potassium alum as a metal salt was excluded from the powdery mixture and the amount of the polymers having the water-absorbing property and/or the water-swelling property was increased in an amount equal to the amount of the excluded metal salt.

COMPARATIVE EXAMPLE 2

A dressing was prepared in the same manner as in Example 2 except that the metal oxide and metal salts used in Example 2 were excluded from the powdery mixture and the amount of the polymers having the water-absorbing property and/or the water-swelling property was increased in an amount equal to the total amount of the excluded metal oxide and metal salts.

COMPARATIVE EXAMPLE 3

A dressing having a γ-ray-irradiated adhesive layer was prepared in the same manner as in Example 3 except that the metal oxide and metal salts used in Example 3 were excluded from the powdery mixture and the amount of the polymers having the water-absorbing property and/or the water-swelling property was increased in an amount equal to the total amount of the excluded metal oxide and metal salts, and that in place of the high-cis-polyisoprene, the same amount of a high molecular weight polyisobutylene (viscosity-average molecular weight: 990,000) was used to prepare a rubber-based adhesive.

COMPARATIVE EXAMPLE 4

A dressing having a γ-ray-irradiated adhesive layer was prepared in the same manner as in Example 4 except that the metal oxide and metal salts used in Example 4 were excluded from the powdery mixture and the amount of the polymers having the water-absorbing property and/or the water-swelling property was increased in an amount equal to the total amount of the excluded metal oxide and metal salts, and that in place of natural rubber, the same amount of a high molecular weight polyisobutylene (viscosity-average molecular weight: 990,000) was used to prepare a rubber-based adhesive.

COMPARATIVE EXAMPLE 5

A dressing having a size of 10 cm by 10 cm was prepared in the same manner as in Example 5 except that the groove formation using heated rolls for press molding was omitted.

According to the method described below, the dressings prepared in the Examples and Comparative Examples above were subjected to a water absorption test, in which the water absorption of each dressing in physiological saline was measured after immersions for a predetermined periods of time. The results obtained are shown in FIGS. 8 to 12.

Water Absorption Measurement

The dressings (1.5 mm thick) were cut into round samples having a diameter of 20 mm, and the samples were separately immersed in 100 ml of physiological saline having a temperature of 37° C. after the separator was stripped from each sample. The water absorption of each sample was measured by taking out the sample from the physiological saline at predetermined time intervals and calculating the weight increase of the sample using the following equation:

Water absorption $(\%) = (W_2 - W_1)/W_1 \times 100$ wherein $W_1$ is the weight of the sample before immersion and $W_2$ is the weight of the sample after immersion.

Figure 12:
FIG. 12 is a graph showing absorption characteristic in physiological saline of the dressings obtained in Examples 2 and 6.

As is apparent from FIGS. 8 to 11, the dressings of the Examples exhibited far better water absorption properties than the dressings of Comparative Examples. FIG. 12, which shows a difference in water absorption between two dressings obtained using powdery mixtures having different average particle diameters, indicates that dressings prepared using powdery mixtures having smaller average particle diameters have better water absorption properties.

Figure 13:
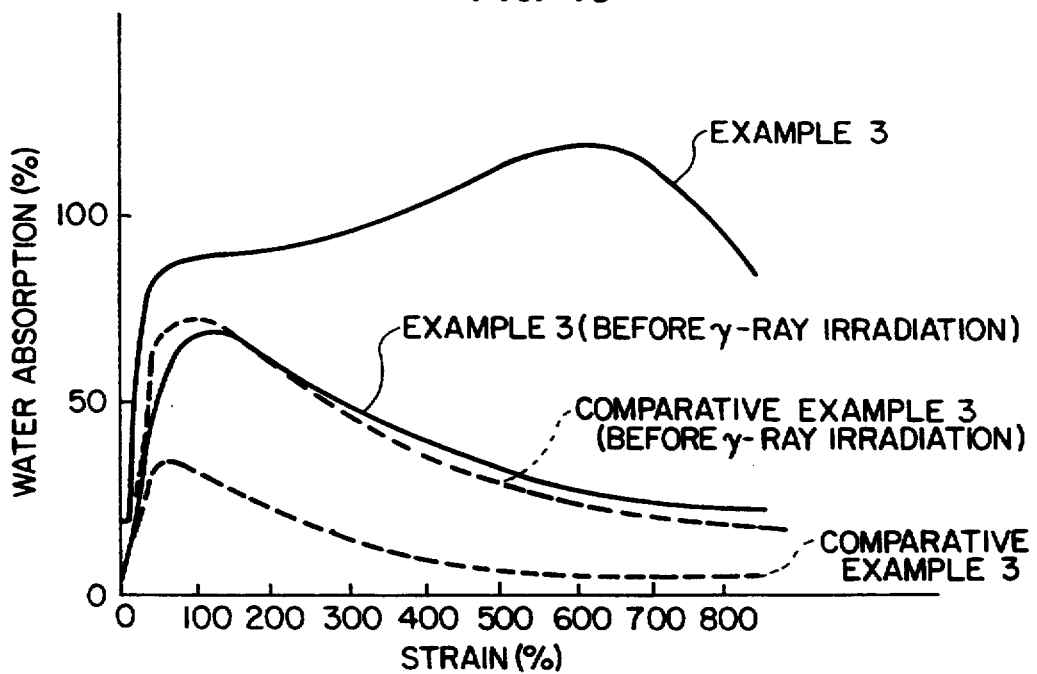
FIG. 13 is a graph showing stress-strain curves of the dressings obtained in Example 3 and Comparative Example 3.

On the other hand, FIG. 13 shows stress-strain curves obtained by solvent-extracting the adhesive layers in the dressings prepared in Example 3 and Comparative Example 3 and subjecting rubbers obtained from the extracts to a stress-strain test. The stress-strain curve for the rubber obtained from the dressing of Example 3 shows that the strength of the rubber had been improved significantly by irradiation with γ-rays. It can be understood from the results that irradiation treatment such as γ-ray irradiation is effective in improving water absorption and preventing the adhesive layer from flowing out.

A practical test was further conducted in which each of the dressings obtained in Example 5 and Comparative Example 5 was applied to a person on the back and the person took a bath. As a result, the edge parts of the adhesive layer of the comparative dressing swelled upon bathing to foul clothes, whereas the dressing of Example 5 was free from the phenomenon.

As described in the examples above, due to the specific construction of the dressing of the present invention, when the dressing is applied to the body at its wounded site or other site, the adhesive layer of the dressing rapidly absorbs an exudate from the wound or other body fluids and, as a result, metal ions are released from the metal oxide or metal salt contained in the adhesive layer and the metal ions form ionic or coordinate bonds to the polymer having the water-absorbing property and/or the water-swelling property, thereby improving the adhesion of the adhesive layer and enabling the adhesive layer to exhibit its water-absorbing or swelling ability while maintaining the shape retention property which is a property originally possessed by the adhesive layer.

Furthermore, since the adhesive layer in the dressing of the present invention shows good adhesion when the dressing is applied to a wounded site or other site of the body, the adhesive layer can efficiently absorb an exudate from the wound or other body fluids without allowing such body fluids to reside on the surface of the wounded site or other site covered with the dressing. Therefore, adhesion to the body can be maintained and the wounded site or other site of the body covered with the dressing can be kept hygienic. Moreover, because the adhesion of the adhesive layer to the body is appropriate, the dressing after use can be stripped safely without damaging the skin of the body part to which the dressing has been applied.

While the invention has been described in detail and with reference to specific embodiments thereof, it will be apparent to one skilled in the art that various changes and modifications can be made therein without departing from the spirit and scope thereof.

What is claimed is:

1. A dressing comprising:
   a backing having a first side and a second side; and
   a continuous adhesive layer formed on said first side of said backing,
   wherein said backing is moisture-permeable and said continuous adhesive layer comprises an adhesive composition comprising a rubber-based adhesive, a polymer having at least one of a water-absorbing property or a water-swelling property, and a water soluble metal salt selected from the group consisting of aluminum salt, calcium chloride, copper sulfate and combinations thereof, said polymer containing a functional group having an ability to form at least one of a salt or a coordination compound whereby said polymer forms ionic or coordinate bonds to metal ions generated from said water soluble metal salt by contact with wound exudate or body fluid to enable the adhesive layer to absorb said wound exudate or body fluid, wherein said rubber-based adhesive contains polyisobutylene as the base material and further contains at least one member selected from the group consisting of polyisoprene, natural rubber, polybutadiene, polyethylene, polypropylene, and an ethylene-propylene copolymer and wherein, said adhesive layer has been subjected to irradiation treatment.

2. A dressing as claimed in claim 1, wherein said backing has a moisture permeability of from 300 to 5,000 g/m$^2$·24 hr.

3. A dressing as claimed in claim 1, further comprising one of a nonwoven and woven fabric laminated with the backing on the second side of said backing, said second side being opposite the adhesive layer.

4. A dressing as claimed in claim 1, wherein said aluminum salt comprises at least one member selected from the group consisting of alum, burnt alum, aluminum sulfate, aluminum lactate, aluminum salicylate, and aluminum nitrate.

5. A dressing as claimed in claim 1, wherein said adhesive composition further comprises at least one of a metal salt, a metal hydroxide or a metal oxide which are sparingly soluble in water.

6. A dressing as claimed in claim 5, wherein said at least one of the metal salt, the metal hydroxide or the metal oxide sparingly soluble in water comprises at least one member selected from the group consisting of aluminum hydroxide, aluminum phosphate, aluminum citrate, calcium hydroxide, calcium carbonate, calcium oxalate, calcium phosphate, calcium oxide, aluminum oxide, zinc oxide, copper oxide, and silver oxide.

7. A dressing as claimed in claim 1, wherein said polymer having the at least one of the water-absorbing property or water-swelling property and said water soluble metal salt are added to the adhesive composition in the form of a powder, the average particle diameter of the whole particles of the powders being 50 μm or less.

8. A dressing as claimed in claim 1, further comprising a separator covering the surface of the adhesive layer and having a length larger than that of the adhesive layer, said backing being bonded to the upper surface and side parts of the adhesive layer.

9. A dressing obtained by a process which comprises the steps of:
coating a backing in continuous form with an adhesive composition comprising a rubber-based adhesive, a polymer having at least one of a water-absorbing property or a water-swelling property, and a water soluble metal salt selected from the group consisting of aluminum salt, calcium chloride, copper sulfate, and combinations thereof, thereby to form a continuous adhesive layer, wherein said rubber-based adhesive contains polyisobutylene as the base material and further contains at least one member selected from the group consisting of polyisoprene, natural rubber, polybutadiene, polyethylene, polypropylene, and an ethylene-propylene copolymer, subjecting said adhesive layer to irradiation, applying a separator to an exposed surface of the continuous adhesive layer, thereby to form a three-layered structure, forming a groove on the three-layered structure by pressing the three-layered structure with one of a mold or a roll having a projection, and cutting the resulting three-layered structure at the grooved part, thereby to produce the dressing, wherein said backing is moisture-permeable, said polymer containing a functional group having an ability to form at least one of a salt and a coordination compound.

* * * * *